(12) United States Patent
Sklavounos et al.

(10) Patent No.: US 6,825,327 B2
(45) Date of Patent: Nov. 30, 2004

(54) PROCESS FOR PREPARING 4"-SUBSTITUTED-9-DEOXO-9A-AZA-9A-HOMOERYTHROMYCIN A DERIVATIVES

(75) Inventors: Constantine Sklavounos, Waterford, CT (US); John L. Tucker, Niantic, CT (US); Lulin Wei, Salem, CT (US); Kerry P. Mahon, Arlington, MA (US); Philip Hammen, East Haddam, CT (US); Joanna T. Negri, Mystic, CT (US); Richard S. Lehner, Ledyard, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/133,472

(22) Filed: Apr. 25, 2002

(65) Prior Publication Data
US 2003/0064939 A1 Apr. 3, 2003

Related U.S. Application Data
(60) Provisional application No. 60/287,203, filed on Apr. 27, 2001.

(51) Int. Cl.$^7$ .......................... C07H 1/00; C07H 17/08
(52) U.S. Cl. .................................. 536/7.4; 536/18.5
(58) Field of Search ........................... 536/7.4, 18.5

(56) References Cited

U.S. PATENT DOCUMENTS

| | | | |
|---|---|---|---|
| 4,328,334 A | 5/1982 | Kobrehel et al. | 536/7.4 |
| 4,474,768 A | 10/1984 | Bright | 424/180 |
| 4,512,982 A | 4/1985 | Hauske et al. | 514/29 |
| 4,517,359 A | 5/1985 | Kobrehel et al. | 536/7.4 |
| 4,518,590 A | 5/1985 | Hauske et al. | 514/29 |
| 5,441,939 A | 8/1995 | Yang | 514/29 |
| 5,869,629 A * | 2/1999 | Jasanda et al. | 536/7.2 |

FOREIGN PATENT DOCUMENTS

| | | | |
|---|---|---|---|
| EP | 0508699 | 10/1992 | C07H/17/08 |
| EP | 0549040 | 6/1993 | C07H/17/08 |
| WO | WO 9856802 | 12/1998 | C07H/17/08 |

* cited by examiner

Primary Examiner—Elli Peselev
(74) Attorney, Agent, or Firm—Peter C. Richardson; Gregg C. Benson; B. Timothy Creagan

(57) ABSTRACT

The invention relates to processes for preparing compounds of formula 1

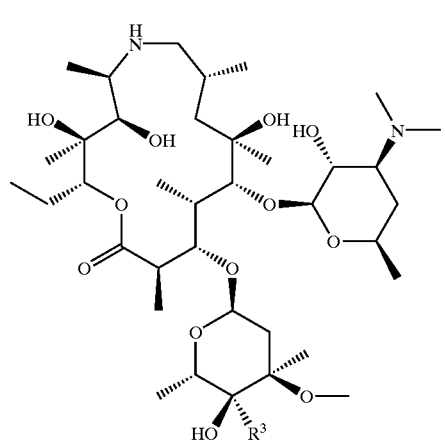

wherein $R^3$ is as defined herein, and to pharmaceutically acceptable salts thereof, as well as intermediates useful in such processes. The compounds of formula 1 are antibacterial agents that may be used to treat various bacterial and protozoa infections. The invention also relates to pharmaceutical compositions containing compounds prepared by the processes of the invention and to methods of treating bacterial protozoa infections by administering such compounds.

57 Claims, No Drawings

PROCESS FOR PREPARING 4"-SUBSTITUTED-9-DEOXO-9A-AZA-9A-HOMOERYTHROMYCIN A DERIVATIVES

CROSS REFERENCE TO RELATED APPLICATION

This application claims benefit of the filing of U.S. 60/287,203 filed on Apr. 27, 2001.

BACKGROUND OF THE INVENTION

This invention relates to processes for preparing C-4" substituted derivatives of 9-deoxo-9a-aza-9a-homoerythromycin A (hereinafter, "azalide(s)") that are useful as antibacterial and antiprotozoal agents in mammals, including man, as well as in fish and birds. This invention also relates to processes for preparing stable intermediates of the subject azalides, as well as to a crystalline salt of an intermediate in the process for preparing the subject azalides. This invention also relates to pharmaceutical compositions containing the novel compounds made by the subject processes and to methods of treating bacterial infections and protozoa infections in mammals, fish and birds by administering the novel compounds produced by the subject processes to mammals, fish and birds requiring such treatment.

Macrolide antibiotics are known to be useful in the treatment of a broad spectrum of bacterial infections and protozoa infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Like azithromycin and other macrolide antibiotics, the macrolide compounds of the present invention possess potent activity against various bacterial infections and protozoa infections as described below.

The production of the subject azalides at commercial scale has presented several difficulties, including, but not limited to, poor yields and instability of some synthetic intermediates, as well as the presence of undesirable impurities.

SUMMARY OF THE INVENTION

The present invention relates to a process for preparing a compound of the formula 1

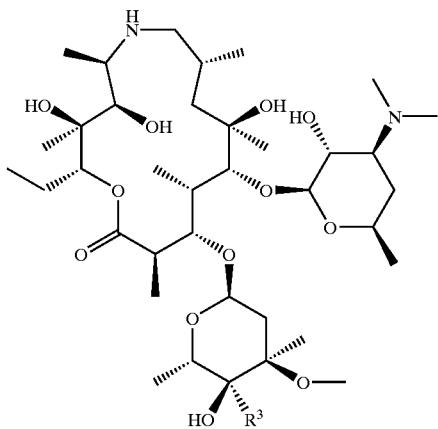

or a pharmaceutically acceptable salt thereof, which comprises:

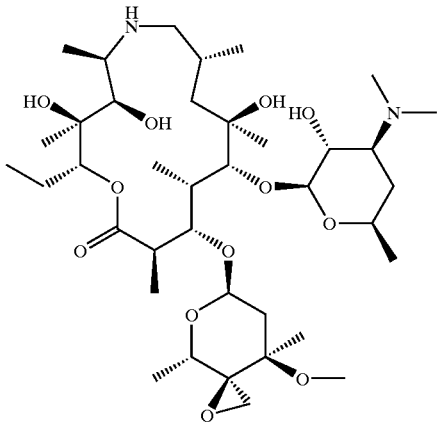

reacting a compound of formula 2 with an amine of the formula $HNR^8R^{15}$, in an organic solvent comprising isopropanol;
wherein the reaction is carried out at a temperature of at least about 40° C.;
wherein:
$R^3$ is $—CH_2NR^8R^{15}$;
$R^8$ is $C_1–C_{10}$ alkyl; and
$R^{15}$ is H or $C_1–C_{10}$ alkyl.

In a preferred embodiment of the process, $R^8$ is propyl and $R^{15}$ is H. In a particularly preferred embodiment, $R^8$ is n-propyl and $R^{15}$ is H.

In a particularly preferred embodiment, the organic solvent is isopropanol.

In another preferred embodiment, the invention relates to a process for

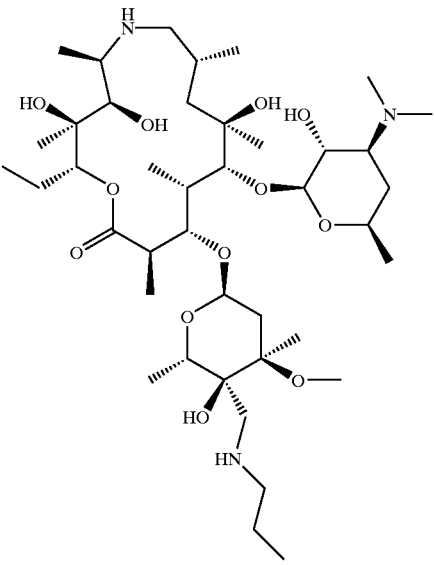

preparing a compound of the formula 1a or a pharmaceutically acceptable salt thereof,
by reacting a compound of formula 2 with n-propylamine in an organic solvent comprising isopropanol; wherein the reaction is carried out at a temperature of at least about 40° C. In a particularly preferred embodiment thereof, the organic solvent is isopropanol.

It is to be noted that the terms "solution" and "mixture", as used herein, unless otherwise indicated, are used interchangeably without regard to the state of dispersion of the components thereof. The phrase "organic solvent comprising isopropanol" as used herein, unless otherwise indicated, means a non-aqueous solvent or mixture of non-aqueous solvents, wherein at least one solvent is isopropanol. In this application, the term "compound of formula 1" includes both the compound of formula 1 and the compound of formula 1a. The compound of formula 1a is a particularly preferred embodiment of the compound of formula 1, to which all of the embodiments and preferred embodiments of the processes described herein apply.

In an embodiment of the processes described herein, the temperature is less than about 95° C., and in a preferred embodiment thereof, the temperature is less than about 80° C. In a more preferred embodiment thereof, the temperature is from about 50° C. to about 76° C. In a particularly preferred embodiment thereof, the temperature is from about 50° C. to about 55° C.

In a preferred embodiment of the processes described herein, the reaction is carried out at about atmospheric pressure. In this application, the term "atmospheric pressure" means a pressure within the normal range of meteorologic atmospheric pressure for a particular altitude, while the term "elevated pressure" means a pressure above atmospheric pressure. In another embodiment of the processes described herein, the reaction is carried out at elevated pressure. In another embodiment of the invention, triethylamine may be present in addition to isopropanol.

In addition to applicants' preferred embodiments, the reaction of the compound of formula 2 with an amine to produce the compound of formula 1 has been successfully performed in solvents other than those comprising isopropanol. Accordingly, this invention also relates to a method for preparing a compound of formula 1 by reacting a compound of formula 2 with an amine of the formula $HNR^8R^{15}$, in an organic solvent, wherein the solvent is selected from the group consisting of benzyl alcohol, acetone, methylisobutylketone, DMSO, t-butanol, n-butanol, diisopropylether, a mixture of MTBE and DMF, and combinations thereof, wherein the reaction is carried out at a temperature of at least about 40° C. The reaction may be carried out at elevated pressures, but is preferably carried out at about atmospheric pressure. In a further embodiment thereof, the reaction is accelerated by the addition of a catalytic amount of a Lewis acid. In an embodiment thereof, the Lewis acid is a reagent such as magnesium bromide, potassium iodide, lithium perchlorate, magnesium perchlorate, lithium tetrafluoroborate, pyridinium hydrochloride, or tetrabutylammonium iodide. Preferably, the Lewis acid is magnesium bromide.

In an embodiment of the processes described herein, the molar amount of amine is at least about five times the molar amount of the compound of formula 2. In another embodiment of the processes described herein, the concentration of amine in isopropanol is at least about 5 molal. In a particularly preferred embodiment, the concentration of n-propylamine is approximately 6–7 molal in isopropanol.

In an embodiment of the above processes, the compound of formula 2 is reacted with the amine for at least about 24 hours. In a preferred embodiment thereof, the molar amount of the amine is at least about five times the molar amount of the compound of formula 2 and the compound of formula 2 is reacted with the amine for at least about 24 hours. In a more preferred embodiment thereof, the temperature is from about 50° C. to about 80° C. In a still more preferred embodiment thereof, the molar amount of the amine is about twenty times the molar amount of the compound of formula 2, the concentration of amine in isopropanol is about 6 molal, and the compound of formula 2 is reacted with the amine for at least about 24 hours at a temperature of from about 50° C. to about 55° C.

Another embodiment of the processes described herein further comprises crystallizing the free base form of the compound of formula 1. In an embodiment, the free base form of the compound of formula 1 is crystallized from an aqueous solvent mixture. In a preferred embodiment thereof, the aqueous solvent mixture comprises water and a non-aqueous solvent selected from the group consisting of methanol, ethanol, isopropanol and acetone. In another embodiment the free base form of the compound of formula 1 is crystallized from an organic $(C_6-C_{10})$alkane solvent or mixture of such organic alkane solvents. In a preferred embodiment thereof, the compound of formula 1 is crystallized by heating the compound together with the alkane solvent followed by cooling to effect crystallization. In a preferred embodiment thereof, the organic $(C_6-C_{10})$alkane solvent is selected from heptane or octane, most preferably heptane. In another embodiment, as described below, the free base is prepared from an acid addition salt of the compound of formula 1. It is to be understood that "alkane" as used herein, unless otherwise indicated, includes saturated monovalent hydrocarbons having straight, cyclic or branched moieties, or mixtures thereof.

In a further embodiment of the processes described herein, an acid addition salt of the compound of formula 1 is prepared by treating the compound of formula 1 with a solution comprising an acid in a water-miscible solvent. In a preferred embodiment thereof, the acid solution is added to a solution comprising the compound of formula 1 and water. In a more preferred embodiment thereof, the acid is phosphoric acid, L-tartaric acid or dibenzoyl-D-tartaric acid. In a particularly preferred embodiment thereof, the acid is phosphoric acid. In another more preferred embodiment thereof, the solvent comprises ethanol. In another preferred embodiment thereof, the above processes further comprise isolating the acid addition salt of the compound of formula 1.

In an embodiment, the processes described herein produce a compound of formula 1 which is at least 90% pure, more preferably at least 95% pure, and most preferably at least 98% pure. In particular, the processes of the invention produce a compound of formula 1 having a purity profile suitable for use of the compound of formula 1 in the preparation of formulations for parenteral administration. The requirements of parenteral formulations are well-known in the art, e.g.: exceptional purity and small particle size in solution, and formulated for sterility and the elimination of pyrogens (see, *Remington's Pharmaceutical Sciences*, Mack Publishing Company, Easton, Pa., 18th Edition, Gennaro, ed. (1990), pages 1545–1580.

In another preferred embodiment thereof, the above processes further comprise treating the acid addition salt of the compound of formula 1 with a base in a mixture of water and a nonpolar solvent, to yield the free base form of the compound of formula 1. In a more preferred embodiment thereof, the base is a dibasic carbonate salt, and in a particularly preferred embodiment, the dibasic carbonate salt is potassium carbonate. In another more preferred embodiment thereof, the nonpolar solvent is dichloromethane. In still another embodiment, the process further comprises crystallization of the free base form of the compound of formula 1 as described above, and the further embodiments relating thereto which are described above.

This invention also relates to a process for preparing a compound of formula 2 which comprises:

(a) reacting the free base form of a compound of formula 3

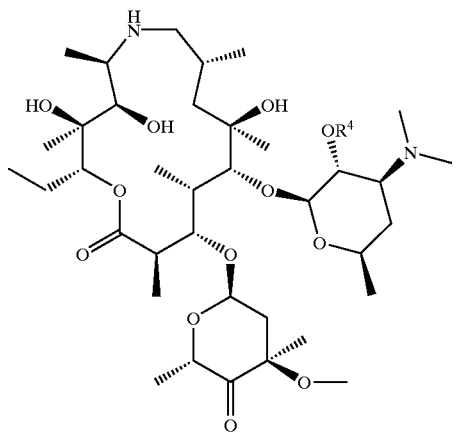

with a sulfonium methylide ion;

(b) quenching the reaction of step (a) with an aqueous weak acid and partitioning the product into a non-aqueous solution; and (c) deprotecting the product of step (b) to yield the compound of formula 2;

wherein $R^4$ is a hydroxy-protecting group.

In an embodiment, the above process further comprises isolation of the compound of formula 2. In a preferred embodiment thereof, the compound of formula 2 is isolated in the form of a hydrate, more preferably, the monohydrate. In an embodiment thereof, the water content is determined by the Karl-Fischer method. In an embodiment thereof, the hydrate is obtained from a mixture containing the compound of formula 2 and a solvent or solvent mixture selected from acetone, acetone/water, acetone/heptane and MTBE/heptane. In other embodiments, the compound of formula 2 is isolated as its acetate salt, L-tartrate salt or dibenzoyl-D-tartrate salt.

This invention relates to the monohydrate of the compound of formula 2. In a preferred embodiment of the above process, $R^4$ is benzyloxycarbonyl.

In another preferred embodiment of the above process, step (a) is carried out at a temperature of from about –80° C. to about –45° C.

In a another embodiment, the above process, the free base form of the compound of formula 3 is prepared from an acid addition salt of the compound of formula 3. In a preferred embodiment thereof, the acid addition salt is a trifluoroacetic acid addition salt. In other embodiments of the above processes, the acid addition salt of the compound of formula 3 is selected from a dibenzoyl-D-tartrate salt, a L-tartrate salt, or a phosphate salt. The acid addition salts of the compounds disclosed herein are readily prepared by conventional means.

In an embodiment of the above process, the sulfonium methylide is dimethylsulfonium methylide. In a preferred embodiment thereof the dimethylsulfonium methylide is prepared by reacting a trimethylsulfonium halide or sulfonate with a strong base. In a more preferred embodiment thereof, a trimethylsulfonium halide is used, which is preferably trimethylsulfonium bromide. In another more preferred embodiment thereof, the trimethylsulfonium halide is reacted with the strong base in an inert organic solvent or mixtures thereof. In a particularly preferred embodiment thereof, the inert organic solvent is an ether solvent, which is most preferably tetrahydrofuran, or a mixture of tetrahydrofuran and dichloromethane.

In an embodiment, step (c) comprises catalytic hydrogenation where $R^4$ is benzyloxycarbonyl. In a preferred embodiment thereof, the catalyst for the hydrogenation is a palladium/carbon catalyst. In a particularly preferred embodiment, the palladium/carbon catalyst is 10% Pd/C (Johnson-Matthey type A402028-10). In a further embodiment of step (c), the product of step (b) is deprotected by catalytic transfer hydrogenation, preferably with ammonium formate, Pd/C in methanol. In a further embodiment, the product of step (b) is trated with Fuller's earth prior to hydrogenation. Suitable solvents for the hydrogenation process are acetone, ethyl acetate, THF, MTBE, isopropanol, ethanol and methanol. A preferred solvent is acetone.

This invention also relates to the 2'-benzyloxycarbonyl protected compound II:

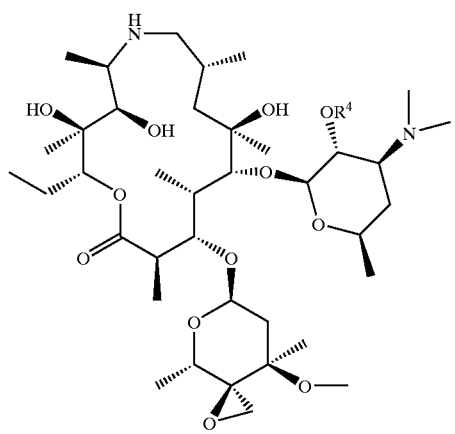

which is obtained by omitting step (c) of the above processes.

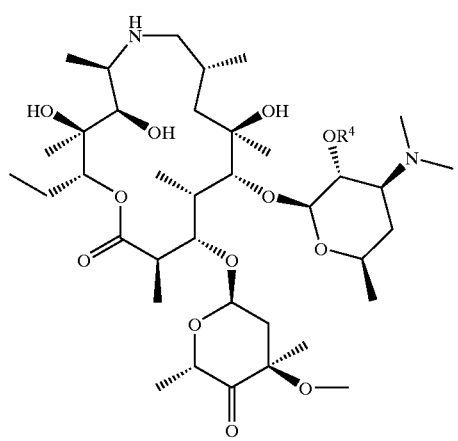

This invention relates to a process for preparing a compound of formula 3 by oxidation of the C-4" hydroxy group of a compound of formula 4

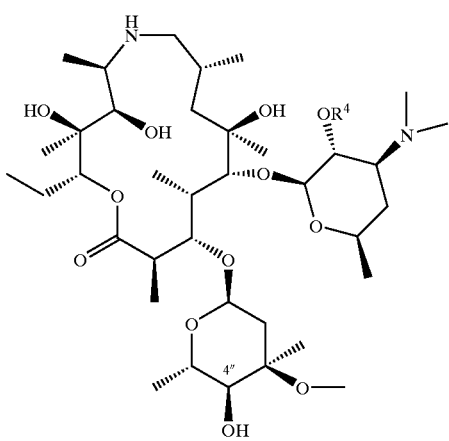

4 wherein R⁴ is a hydroxy protecting group.

In an embodiment, the oxidation is performed by adding dimethylsulfoxide ("DMSO") to a solution comprising the compound of formula 4 and a solvent, cooling the mixture to about −70° C., and then adding trifluoroacetic anhydride, followed by addition of triethylamine. In other embodiments, the DMSO is activated using oxalyl chloride (with or without trimethylsilylacetamide), polyphosphoric acid, pyridine.SO3, or acetic anhydride. In a further embodiment thereof, the temperature is maintained between −70° C. and −60° C. during the addition of trifluoroacetic anhydride. In another embodiment thereof, the solvent is dichloromethane. A particular advantage of the above process is the in situ activation of DMSO in the presence of the reacting alcohol, which avoids the formation of impurities typically encountered in activated DMSO oxidations, which usually involve the introduction of the alcohol to a solution containing activated DMSO.

In an embodiment, the above process further comprises isolating an acid addition salt of the compound of formula 3. In a preferred embodiment the acid addition salt is a dibenzoyl-D-tartrate salt or a phosphate salt. In a particularly preferred embodiment, this invention relates to a process for preparing the trifluoroacetic acid addition salt of a compound of formula 3 which comprises treating the compound of formula 3 with trifluoroacetic acid; and crystallizing the resulting acid addition salt;

wherein R⁴ is a hydroxy-protecting group.

In a preferred embodiment of the above process, R⁴ is benzyloxycarbonyl.

In another preferred embodiment of the above process, the acid addition salt is crystallized from isopropanol.

In still another preferred embodiment of the above process, the acid addition salt is crystallized from a mixture of methylene chloride and methyl tert-butyl ether.

The trifluoroacetic acid addition salts prepared by the processes of this invention are not pharmaceutically acceptable, but provide excellent purification and stability, allowing the storage and transport of appropriate starting materials in the commercial preparation of compounds of formula 1.

In an embodiment of the above process, the compound of formula 4 is prepared by protection of the 2'-hydroxy group of the compound of formula 5

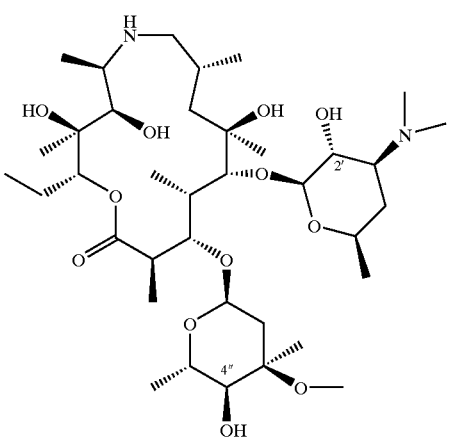

5

In a preferred embodiment, the 2'-hydroxy group is protected with benzyloxycarbonyl. In another preferred embodiment, the compound of formula 5 is reacted with at least two molar equivalents of benzylchloroformate. In a more preferred embodiment, the reaction is carried out in dichloromethane. In a still more preferred embodiment, the dichloromethane is present in at least a 15-fold excess volume relative to the volume of starting material. This invention also relates to a

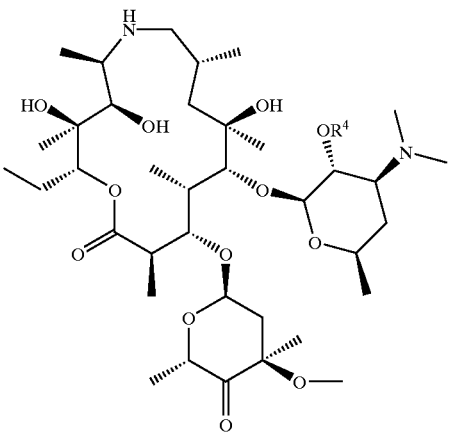

3 trifluoroacetic acid addition salt of the compound of formula 3, wherein R⁴ is benzyloxycarbonyl:

In a preferred embodiment thereof, the salt has the structure shown in formula 3a

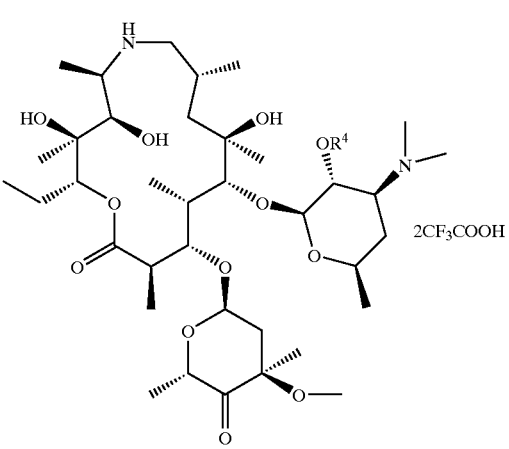

3a wherein R⁴ is benzyloxycarbonyl.

This invention also relates to a dibenzoyl-D-tartrate salt of the compound of formula 3, wherein, $R^4$ is benzyloxycarbonyl.

The term "hydroxy-protecting group", as used herein, unless otherwise indicated, includes acetyl, benzyloxycarbonyl, and various hydroxy-protecting groups familiar to those skilled in the art include the groups referred to in T. W. Greene, P. G. M. Wuts, "Protective Groups In Organic Synthesis," (J. Wiley & Sons, 1991). Preferably, the hydroxy-protecting group $R^4$ is benzyloxycarbonyl ("CBZ").

The term "halo", as used herein, unless otherwise indicated, includes fluoro, chloro, or bromo, and the term "halide" refers to the corresponding mono anions, $F^-$, $Cl^-$, or $Br^-$, respectively.

The term "alkyl", as used herein, unless otherwise indicated, includes saturated monovalent hydrocarbon radicals having straight, cyclic or branched moieties, or mixtures thereof.

The phrase "pharmaceutically acceptable salt(s)", as used herein, unless otherwise indicated, includes salts of acidic or basic groups which may be present in the compounds of the present invention. The compounds prepared by the processes of the present invention that are basic in nature, particularly e.g., the free base form of the compounds of formula 1, are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds prepared by the processes of the present invention that include an amino moiety may form pharmaceutically acceptable salts with various amino acids, in addition to the acids mentioned above.

The term "treatment", as used herein, unless otherwise indicated, includes the treatment or prevention of a bacterial infection or protozoa infection as provided in the method of the present invention.

The present invention includes the compounds of the present invention, and the pharmaceutically acceptable salts thereof, wherein one or more hydrogen, carbon, nitrogen or other atoms are replaced by isotopes thereof. Such compounds may be useful as research and diagnostic tools in metabolism pharmacokinetic studies and in binding assays.

DETAILED DESCRIPTION OF THE INVENTION

The process of the present invention may be carried out according to Schemes 1–4 below and the description that follows. In the following Schemes, unless otherwise indicated, substituents $R^3$, $R^4$, $R^8$ and $R^{15}$ are as defined above.

Scheme 1

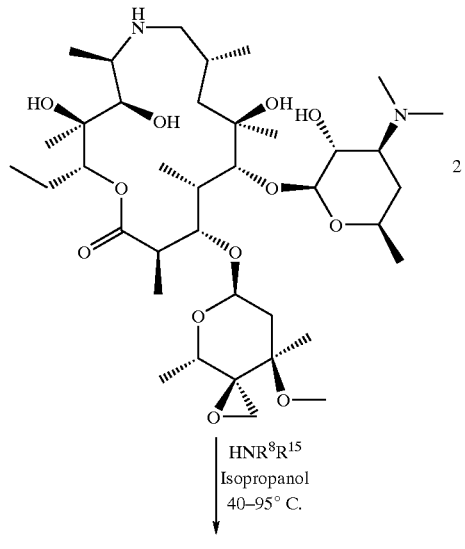

Scheme 2

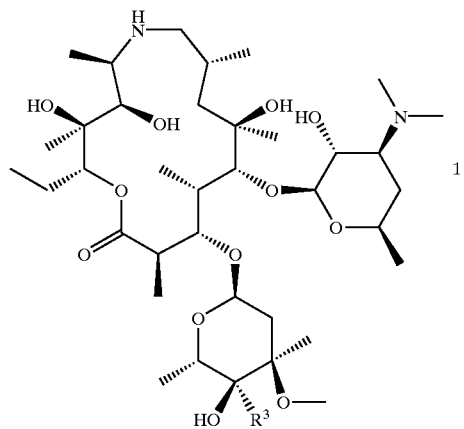

-continued

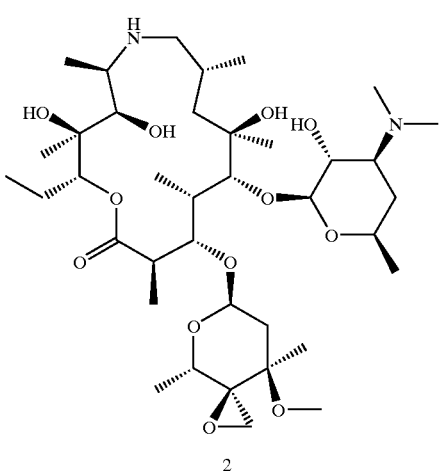

2

Scheme 3

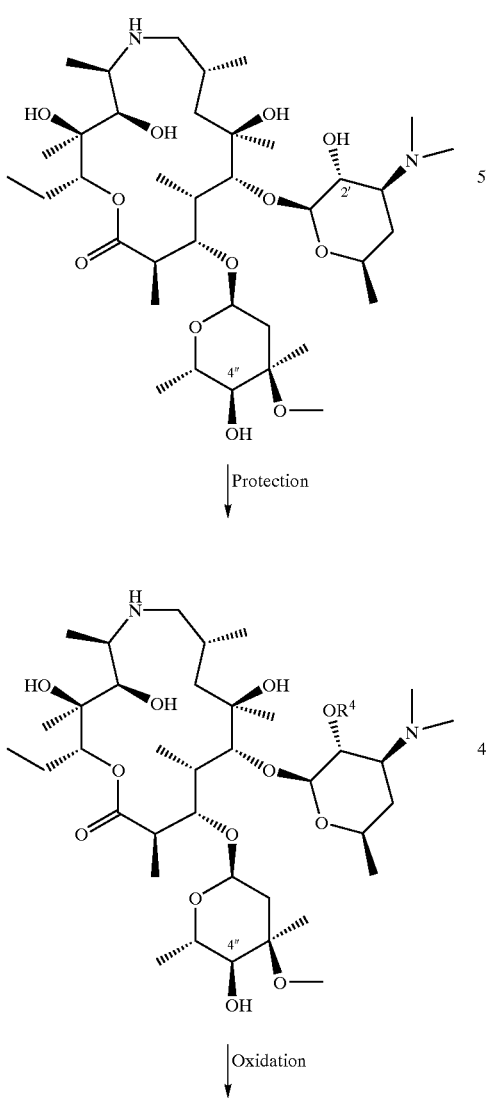

-continued

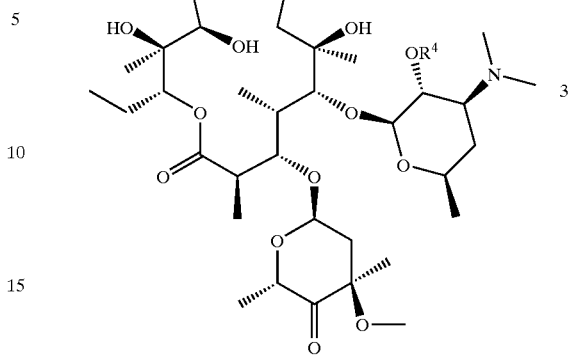

The compound of formula 4, used as a starting material for the processes of the present invention is readily prepared from compound 5, i.e., in which $R^4$ is hydrogen, see, WO 98/56802, and U.S. Pat. Nos. 4,328,334, 4,474,768 and 4,517,359, all of which are incorporated herein by reference in their entirety.

The Schemes given above are illustrative only and are described in further detail below and in the Examples further hereinbelow. In Scheme 1, the epoxide of formula 2 is converted to an amine of formula 1, wherein $R^3$ is —$CH_2NR^{15}R^8$ wherein $R^{15}$ and $R^8$ are as defined above. In the most preferred embodiment of the invention, the amine is n-propylamine, i.e., $R^8$ is n-propyl and $R^{15}$ is H.

To prepare a compound of formula 1, the compound of formula 2 is preferably treated with a compound of the formula $HNR^{15}R^8$, wherein $R^{15}$ and $R^8$ are as defined above, in the presence of an appropriate solvent such as isopropanol, or a mixture of organic solvents comprising isopropanol, preferably at a temperature of from about 40° C. to about 95° C. The most preferred temperature to perform the reaction is from about 50° C. to about 55° C., but higher temperatures may also be used, e.g., 76° C. The most preferred pressure to perform the reaction is at about atmospheric pressure; however, the reaction may also be performed at elevated pressures.

In one previous method of opening the epoxide of formula 2 (see, WO 98/56802, Examples 48, 50, 51 and 70) the 2'-hydroxy group was protected, and the production of the compound of formula 1 (or formula 1a, respectively) required the simultaneous hydrolysis of the protecting group and the amination of the epoxide. This process was not preferred because performing the hydrolysis during the epoxide opening step is inefficient, and isolation of the compound of formula 1 was made more difficult due to the presence of the unhydrolysed protecting group and other impurities. In another previous method, the compound of formula 2 (in which the 2'-hydroxy is not protected), was reacted with pure alkylamine, i.e., without organic solvent. In this case, the reaction proceeded slowly at the normal boiling temperature of n-propylamine (about 48° C.). Consequently, in order to produce an elevated temperature, the reaction was run at elevated pressure, a less preferred feature at commercial scale. (See, WO 98/56802, Example 8 (Preparation 2), having a yield of 11%). In addition, a catalyst was used in the reaction. Applicants made the discovery that a mixture of n-propylamine and isopropanol has a boiling point, at ambient atmospheric pressure, of about 76° C., which allows the reaction to proceed at high yield (over 85%), at a temperature of about 50° C. to 55° C., without the use of a pressurized reaction vessel or catalyst (s). Applicants' method provides high yield (85%) and a better purity profile than earlier methods, and allows a variety of crystallization procedures for both the free base form and acid salts of the compound of formula 1, to afford the compound of formula 1 in highly purified form such as is desirable for use in parenteral formulations.

In Scheme 2, the compound of formula 2 may be prepared by treating the compound of formula 3 with a sulfur methylide, at a temperature of from about −80° C. to about −45° C., followed by removal of the 2'-protecting group by conventional methods, to provide the compound of formula 2. The starting material for the process of Scheme 2 is preferably the trifluoroacetic acid addition salt of the compound of formula 3, which is first converted to the free base form, cooled to low temperature, about −70° C., and then reacted with a low-temperature solution of the sulfur methylide. The sulfur methylide is preferably a dimethylsulfonium methylide, e.g., $(CH_3)_2S^+CH2^-$, prepared by conventional means, e.g., by treating a trimethylsulfonium salt, e.g., $(CH_3)_3SX$, wherein X is halo, preferably bromo, or a sulfonate, more preferably trimethylsulfonium bromide, with an activating agent such as potassium hydroxide, potassium tert-butoxide, sodium tert-butoxide, potassium ethoxide, sodium ethoxide, potassium hexamethyldisilazide (KHMDS) or sodium methoxide, preferably potassium tert-butoxide, in an ether solvent such as THF, or in $CH_2Cl_2$, DMF, or DMSO, or a mixture of two or more of the foregoing solvents. The protecting group is removed by conventional means, e.g., catalytic hydrogenation when $R^4$ is CBZ.

In Scheme 3, the 4" ketone is prepared from the compound of formula 5 in a single-vessel, continuous process. In the first step of the process, the 2' hydroxy group is selectively protected by conventional means, preferably by treating the 2'-hydroxy of formula 5, wherein $R^4$ is hydrogen, with benzylchloroformate in dichloromethane to yield the compound of formula 4 wherein $R^4$ is benzyloxycarbonyl ("CBZ"). Preferably, at least 2 molar equivalents of benzylchloroformate are used, in order to ensure complete conversion of the 2'-hydroxy group to its protected form. Dichloromethane is preferred as solvent, wherein the reaction is performed using at least 15 volumes of dichloromethane relative to the volume of starting material, thus minimizing the formation of bis-CBZ impurities. The compound of formula 4, wherein R4 is CBZ, may be isolated as its dibenzoyl-D-tartrate salt, which allows purging of potential bis-CBZ impurity. However, aqueous extractive workup of the compound of formula 4 is not preferred, because the isolated product is unstable due to the presence of a benzylamine formed by amine alkylation of the compound of formula 4 by benzylchloride (formed by the decomposition of benzylchloroformate). Accordingly, after the protection step the reaction mixture is preferably carried forward directly to the second step without isolation of the compound of formula 4. The second step, which may be carried out in the same vessel as the first step, comprises oxidation of the 4"-hydroxyl group to yield the 4"-ketone of formula 3. The oxidation is preferably an activated-DMSO oxidation as described above, i.e., performed at reduced temperature, e.g., −60 to −70° C., and involving activation of the DMSO in situ by adding trifluoroacetic anhydride to the chilled solution of the compound in DMSO, followed by addition of triethylamine. The reaction mixture is then added to water and gradually warmed to ambient temperature. The mixture is preferably washed in water to yield a solution of the compound of formula 3.

The trifluoroacetic acid salt of the compound of formula 3 may be prepared by washing the reaction mixture of the oxidation step with water, followed by addition of trifluoroacetic acid and then a solvent suitable for crystallization of the salt, for example isopropanol or a mixture of methylene chloride and methyl tert-butyl ether ("MTBE"). Other acid addition salts, such as the dibenzoyl-D-tartrate salt and the phosphate salt, may also be prepared, in a conventional manner. The dibenzoyl-D-tartrate and phosphate salts are useful in the processes of the invention, but are less preferred compared to trifluoroacetic acid.

As shown in Scheme 4, altogether the invention relates to a process for preparing the compound of formula 1 in two stages: in the first stage, the compound of formula 3 is prepared in a single-vessel process involving benzyloxycarbonyl protection of the 2'-hydroxy group of the compound of formula 5 to yield the compound of formula 4, followed directly by oxidation of the 4"-hydroxy group of 4 to yield the ketone of formula 3, which is preferably isolated as its trifluoroacetic acid addition salt. In the second stage, the free base form of the compound of formula 3 (preferably prepared from its trifluoroacetic acid salt) is converted to the 4"-epoxide of formula 2, the 2'-protecting group is removed to restore the 2'-hydroxy, and the epoxide is opened with an amine by heating in a mixture containing isopropanol, to yield the compound of formula 1.

Scheme 4

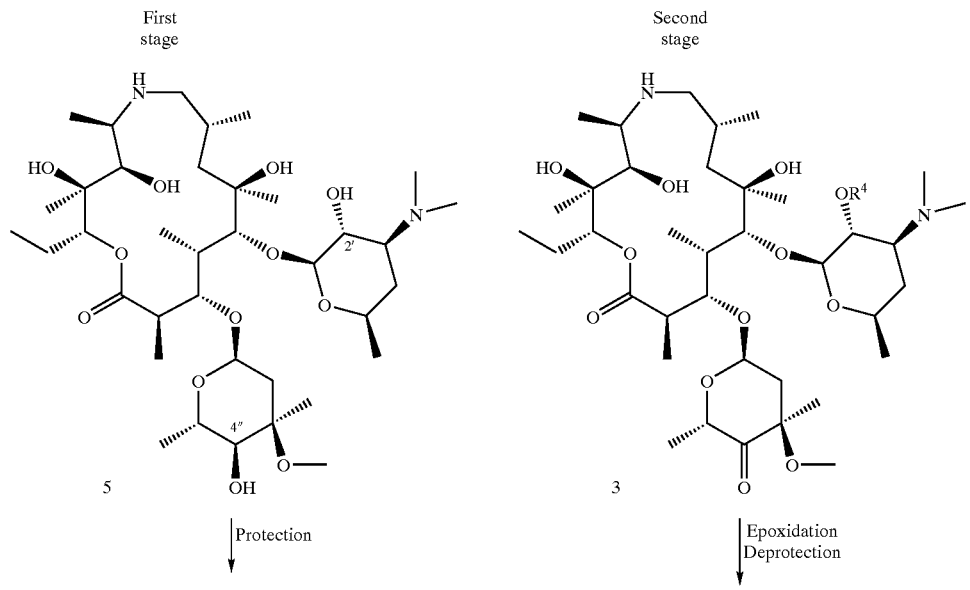

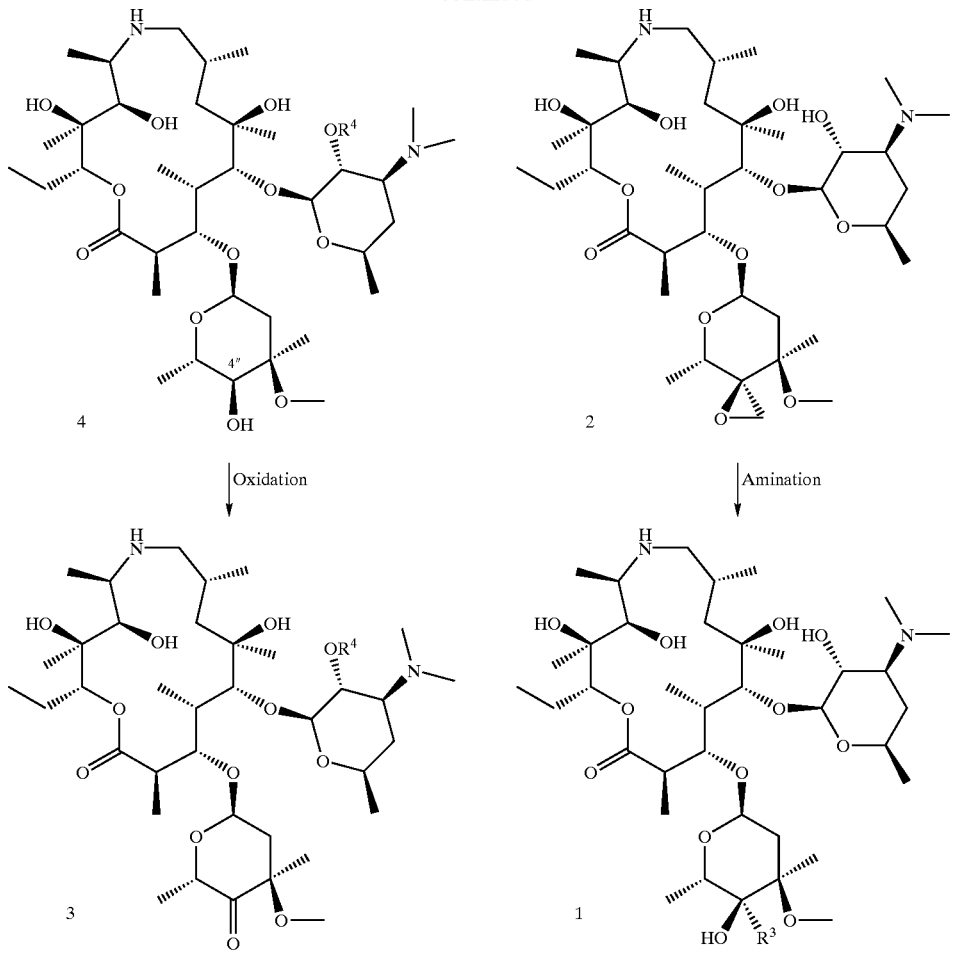

The compounds prepared by the processes of the present invention that are basic in nature are capable of forming a wide variety of different salts with various inorganic and organic acids. Although such salts must be pharmaceutically acceptable for administration to mammals, it is often desirable in practice to initially isolate a compound prepared by the processes of the present invention from the reaction mixture as a pharmaceutically unacceptable salt and then simply convert the latter back to the free base compound by treatment with an alkaline reagent, for use in subsequently reactions or for the preparation of a pharmaceutically acceptable acid addition salt. The acid addition salts of the base compounds prepared by the processes of this invention are readily prepared by treating the base compound with a substantially equivalent amount of the chosen mineral or organic acid in an aqueous solvent medium or in a suitable organic solvent. Upon careful evaporation of the solvent, the desired solid salt is readily obtained. The desired salt can also be precipitated from a solution of the free base in an organic solvent by adding to the solution an appropriate mineral or organic acid. The compounds of formula 1 prepared by the processes of this invention, and the pharmaceutically acceptable salts thereof (hereinafter "the active compounds"), may be administered through oral, parenteral, topical, or rectal routes in the treatment of bacterial and protozoa infections.

In general, the active compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The following Examples further illustrate the method and intermediates of the present invention. It is to be understood that the present invention is not limited to the specific details of the Examples provided below.

EXAMPLE 1

Preparation of (2R,3S,4R,5R,8R,10R,11R,12S,13S, 14R)-13-[(2,6-dideoxy-3-C-meth-3-O-methyl-α-L-ribo-hexopyranosyl)oxy]-2-ethyl-3,4,10-trihydroxy-3,5,8,10,12,14-hexamethyl-11-[[3,4,6-trideoxy-3-(dimethylamino)-2-O-[(phenylmethoxy)carbonyl]-α-D-xylo-hexopyranosyl]oxy]-1-oxa-6-azacyclopentadecan-15-one.

To a solution of 25 kg of (2R,3S,4R,5R,8R,10R,11R,12S, 13S,14R)-13-[(2,6-dideoxy-3-C-meth-3-O-methyl-α-L-ribo-hexopyranosyl)oxy]-2-ethyl-3,4,10-trihydroxy-3,5,8, 10,12,14-hexamethyl-11-[[3,4,6-trideoxy-3-(dimethylamino)-α-D-xylo-hexopyranosyl]oxy]-1-oxa-6-azacyclopentadecan-15-one in 425 L of methylene chloride cooled to 0–5° C. was added a solution of 13.7 kg benzylchloroformate in 25 L of methylene chloride, at a rate to maintain the temperature under 5° C. The resultant mixture was agitated at this temperature for three hours and then concentrated to 148 L to obtain a dry solution containing approximately 26.6 kg (90%) of product (by HPLC—Waters Symmetry C8, 15 cm×3.9 mm I.D. column, 25 mM potassium phosphate buffer (pH 7.5):Acetonitrile:Methanol (35:50:15) mobile phase, 2.0 ml/min flow rate, electrochemical detection. Retention Time=8.2 minutes). This mixture was used directly in Example 2.

EXAMPLE 2

Preparation of (2R,3S,4R,5R,8R,10R,11R,12S,13S, 14R)-13-[(2,6-dideoxy-3-C-meth-3-O-methyl-α-L-ribo-hexopyranosyl)oxy]-2-ethyl-3,4,10-trihydroxy-3,5,8,10,12,14-hexamethyl-11-[[3,4,6-trideoxy-3-(dimethylamino)-2-O-[(phenylmethoxy)carbonyl]-α-D-xylo-hexopyranosyl]oxy]-1-oxa-6-azacyclopentadecan-15-one, trifluoroacetic acid salt.

To the solution obtained in Example 1 was added 58.6 kg dimethylsulfoxide ("DMSO") followed by cooling to −70° C. While maintaining the temperature between −70 and −60° C., 16 kg trifluoroacetic anhydride was added and the mixture was stirred for 30 minutes, then 17.2 kg triethylamine was added, and the resultant mixture was stirred for an additional 30 minutes. The reaction mixture was added to 175 L of water and after gradual warming to ambient temperature the layers were separated. The organic layer was washed twice with 170 L of water and concentrated to approximately 100 L. Next, 7.8 kg of trifluoroacetic acid was added, followed by 236 L isopropanol, and the mixture was concentrated to crystallize out 29.5 kg (87.9%) product which was 98% pure by HPLC.
Analytical data: mp=187–192° C. Elemental Analysis. (Calculated for $C_{49}H_{76}F_6N_2O_{18}$: C, 53.74; H,6.99; F, 10.41; N, 2.56; Found: C, 53.87; H, 6.99; F, 10.12; N, 2.59. HPLC System: same as Example 1; retention Time=9.5 minutes. X-Ray Powder Diffraction (d space): 6.3, 8.3, 8.8, 9.4, 10.8, 11.8, 12.6, 13.0, 14.3, 15.4, 15.9, 16.4, 17.1, 17.4, 17.8, 18.1, 19.1, 19.8, 20.4, 21.1, 21.5, 21.7, 22.8, 23.4, 24.0.

EXAMPLE 3

Preparation of (2R,3S,4R,5R,8R,10R,11R,12S,13S, 14R)-2-ethyl-3,4,10-trihydroxy-13-[[(3S,4S,6R8R)-8-methoxy-4,8-dimethyl-1,5-dioxaspiro[2.5]oct-6-yl]oxy]3,5,8,10,12,14-hexamethyl-11-[[3,4,6-trideoxy-3-(dimethylamino)-2-O-[(phenylmethoxy) carbonyl]-α-D-xylo-hexopyranosyl]oxy]-1-oxa-6-azacyclopentadecane-15-one.

(a) A solution of 109 kg of the product of Example 2 in 327 L of methylene chloride was treated with a solution of 27.5 kg potassium carbonate in 327 L of water. The layers were separated, the aqueous layer was washed with 327 L of methylene chloride, and the combined organic layers were dried and evaporated to about 327 L, and cooled to −70° C.

(b) In a separate vessel, a suspension of 29.7 kg of trimethylsulfonium bromide in 436 L of tetrahydrofuran ("THF") was evaporated to approximately 170 L, cooled to −12° C. and treated with 36.8 kg of potassium tert-butoxide for 75 minutes at −10 to −15° C. This mixture was then added to the methylene chloride solution of step (a), over a period of about 30 minutes, while maintaining the temperature at −70 to −80° C., and the resultant mixture was allowed to warm up to −65° C. and stirred for at least 1 hour. The mixture was then added to a solution of 55.4 kg of ammonium chloride in 469 L of water. After stirring the mixture at 15–25° C. for 15 minutes, the layers were separated, the aqueous layer was washed with 360 L methylene chloride and the combined organic layers were evaporated to approximately 227 L. To the resultant mixture was added 750 L of acetone. Finally the mixture was evaporated to 227 L of solution containing approximately 70.1 kg (80%) of the title product (by HPLC-HPLC System: MetaSil AQ C18 column (from MetaChem, part number 0520-250X046), 50 mM potassium phosphate buffer (pH 8.0):Acetonitrile:Methanol (30:60:10) mobile phase, 1.0 ml/min flow rate, electrochemical detection. Retention Time=31.1 minutes). This mixture was used directly in Example 4.

EXAMPLE 4

Preparation of (2R,3S,4R,5R,8R,10R,11R,12S,13S, 14R)-2-ethyl-3,4,10-trihydroxy-13-[[(3S,4S,6R8R)- 8-methoxy-4,8-dimethyl-1,5-dioxaspiro[2.5]oct-6- yl]oxy]-3,5,8,10,12,14-hexamethyl-11-[[3,4,6- trideoxy-3-(dimethylamino)-α-D-xylo- hexopyranosyl]oxy]-1-oxa-6-azacyclopentadecane- 15-one.

The solution containing the product of Example 3 was combined with 11 kg activated carbon, 17.5 kg of 10% palladium on carbon (Johnson-Matthey type A402028-10), and 637 L of acetone. The resultant mixture was treated with hydrogen at 50 psi at 20–25° C. until the reaction was completed and then filtered. The filtrate was concentrated to approximately 350 L and then 1055 L of water was added over 90 minutes. The crystallized product was collected by filtration, washed with a mixture of 132 L of water and 45 L of acetone, and dried to yield 57.5 kg (94.4%) of the title epoxide as a monohydrate (water content by Karl-Fischer method).

Analytical data: HPLC system: same as Example 3; Retention Time=13.3 minutes. X-Ray Powder Diffraction (d space): 6.0, 8.5, 9.4, 11.9, 12.7, 13.4, 15.2, 16.9, 17.5, 18.0, 18.9, 19.4, 19.9, 20.7, 21.2, 21.6, 22.8.

EXAMPLE 5

Preparation of (2R,3S,4R,5R,8R,10R,11R,12S,13S, 14R)-13-[(2,6-dideoxy-3-C-meth-3-O-methyl-4-C- [(propylamino)methyl]-α-L-ribo-hexopyranosyl) oxy]-2-ethyl-3,4,10-trihydroxy-3,5,8,10,12,14- hexamethyl-11-[[3,4,6-trideoxy-3-(dimethylamino)- β-D-xylo-hexopyranosyl]oxy]-1-oxa-6- azacyclopentadecan-15-one, bis phosphoric acid salt.

56 kg of the epoxide monohydrate of Example 4 was combined with 280 L of isopropanol and 108.2 kg of n-propylamine. The mixture was heated at 50–55° C. for thirty hours and then concentrated under vacuum to approximately 112 L. To the concentrate was added 560 L of ethanol and 44.8 L of water. To the resultant mixture was added, over the course of about two hours, 16.8 kg of phosphoric acid in 252 L of ethanol, to crystallize the product. After stirring the resultant suspension for 18 hours, the mixture was filtered, the solid was washed with 28 L of ethanol, and the product dried to yield 64.6 kg (88%) of the title compound (by HPLC-HPLC System: YMC-Pack Pro C18 (YMC Inc. Part #AS-12S03-1546WT), 50 mM potassium phosphate dibasic buffer (pH 8.0):Acetonitrile:Methanol 61:21:18 mobile phase, 1.0 ml/min flow rate, electrochemical detection. Retention Time=26.4 minutes).

EXAMPLE 6

Preparation of (2R,3S,4R,5R,8R,10R,11R,12S,13S, 14R)-13-[(2,6-dideoxy-3-C-meth-3-O-methyl-4-C- [(propylamino)methyl]-α-L-ribo-hexopyranosyl) oxy]-2-ethyl-3,4,10-trihydroxy-3,5,8,10,12,14- hexamethyl-11-[[3,4,6-trideoxy-3-(dimethylamino)- β-D-xylo-hexopyranosyl]oxy]-1-oxa-6- azacyclopentadecan-15-one, free base.

64.6 kg of the product of Example 5 was combined with 433 L of methylene chloride, 433 L of water and 27.6 kg of potassium carbonate. After stirring the mixture for thirty minutes, the layers were separated, and the aqueous layer was washed with 32 L of methylene chloride. The combined organic layers were clarified by filtration and evaporated to approximately 155 L. To the concentrate was added 386 L of heptanes, and the solution was evaporated to about 155 L and cooled to 20–25° C. to effect crystallization. After stirring the mixture for six hours, the solids were collected by filtration, washed with 110 L of heptanes and dried to yield 40.3 kg (77%) of the title compound (by HPLC; same system as in Example 5; Retention time 26.4 minutes).

What is claimed is:

1. A process for preparing a compound of the formula 1

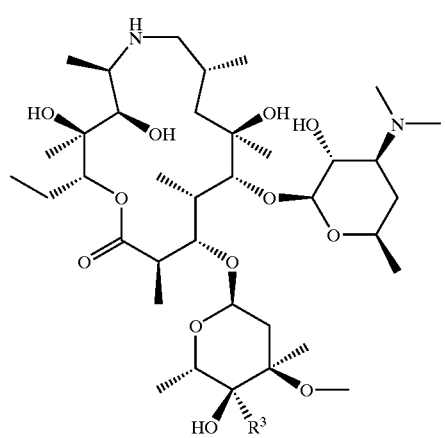

or a pharmaceutically acceptable salt thereof, which comprises reacting a compound of formula 2

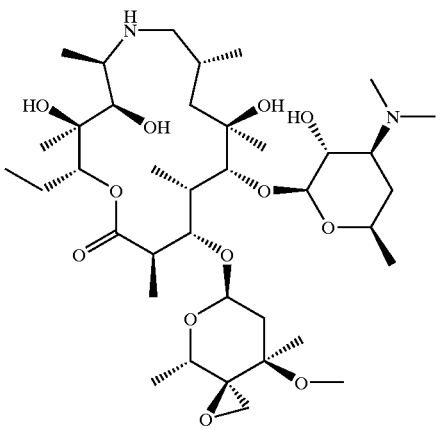

with an amine of the formula HNR⁸R¹⁵, in an organic solven comprising isopropanol;

wherein the reaction is carried out at a temperature of at least about 40° C.;
wherein:
$R^3$ is —$CH_2NR^8R^{15}$;
$R^8$ is $C_1$–$C_{10}$ alkyl;
$R^{15}$ is H or $C_1$–$C_{10}$ alkyl.

2. The process of claim 1, wherein the organic solvent is isopropanol.

3. The process of claim 1, wherein $R^8$ is propyl and $R^{15}$ is H.

4. The process of claim 3, wherein $R^8$ is n-propyl.

5. The process of claim 1, which comprises preparing a compound of the formula 1a

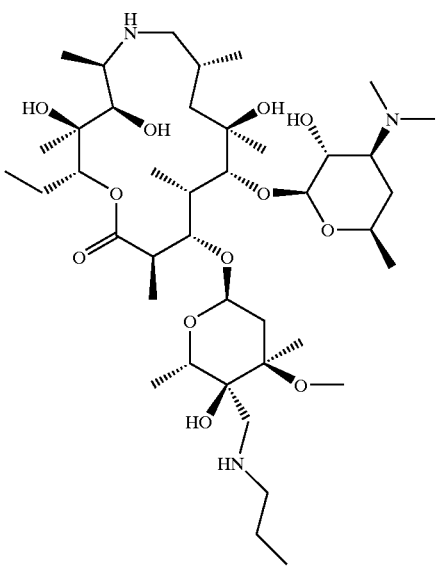

or a pharmaceutically acceptable salt thereof, by reacting a compound of formula 2 with n-propylamin in an organic solvent comprising isopropanol;
wherein the reaction is carried out at a temperature of at least about 40° C.

6. The process of claim 5, wherein the organic solvent is isopropanol.

7. The process of claim 1, wherein the temperature is less than about 95° C.

8. The process of claim 7, wherein the temperature is from about 50° C. to about 76° C.

9. The process of claim 8, wherein the temperature is from about 50° C. to about 55° C.

10. The process of claim 1, wherein the reaction is carried out at about atmospheric pressure.

11. The process of claim 1, wherein the molar amount of amine is at least about five times the molar amount of the compound of formula 1.

12. The process of claim 1, wherein the concentration of amine in isopropanol is at least about 5 molal.

13. The process of claim 8, wherein the molar amount of the amine is at least about five times the molar amount of the compound of formula 2 and the temperature is from about 50° C. to about 55° C.

14. The process of claim 13, wherein the molar amount of the amine is about twenty times the molar amount of the compound of formula 2, the concentration of amine in isopropanol is about 6 molal, and the compound of formula 2 is reacted with the amine for at least about 24 hours.

15. The process of claim 1, which further comprises crystallizing the free base form of the compound of formula 1.

16. The process of claim 15, wherein the free base form of the compound of formula 1 is crystallized from an aqueous solvent mixture.

17. The process of claim 16, wherein the aqueous solvent mixture comprises water and a non-aqueous solvent selected from methanol, ethanol, isopropanol and acetone.

18. The process of claim 15, wherein the free base form of the compound of formula 1 is crystallized from an organic ($C_6$–$C_{10}$) alkane solvent.

19. The process of claim 18, wherein the solvent comprises heptane or octane.

20. The process of claim 1, which further comprises treating the compound of formula 1 with a solution comprising an acid in a water-miscible solvent.

21. The process of claim 20, wherein the acid solution is added to a solution comprising the compound of formula 1 and water.

22. The process of claim 20 wherein the acid is phosphoric acid, L-tartaric acid, or dibenzoyl-D-tartaric acid.

23. The process of claim 20, wherein the solvent comprises ethanol.

24. The process of claim 20, which further comprises isolating the acid salt of the compound of formula 1.

25. The process of claim 24, which further comprises treating the acid addition salt of the compound of formula 1 with a base in a mixture of water and a nonpolar solvent, to yield the free base form of the compound of formula 1.

26. The process of claim 25 wherein the base is a dibasic carbonate salt.

27. The process of claim 26 wherein the dibasic carbonate salt is potassium carbonate.

28. The process of claim 25, wherein the nonpolar solvent is dichloromethane.

29. A process for preparing a compound of formula 2

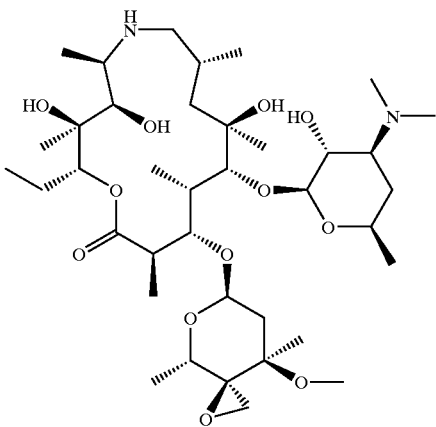

which comprises:
(a) reacting the free base form of a compound of formula 3

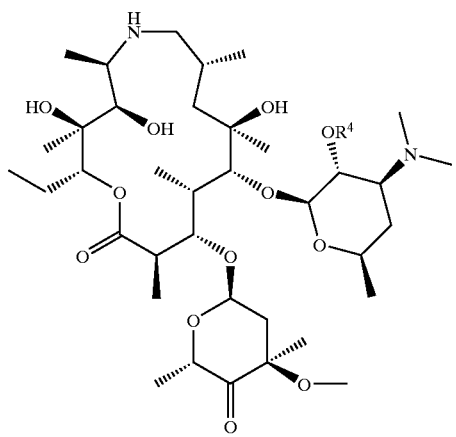

with a sulfonium methylide ion;
(b) quenching the reaction of step (a) with an aqueous weak acid and partitioning the product into a non-aqueous solution; and
(c) deprotecting the product of step (b) to yield the compound of formula 2;
wherein $R^4$ is a hydroxy-protecting group.

30. The process of claim 29, wherein $R^4$ is benzyloxycarbonyl.

31. The process of claim 29, wherein step (a) is carried out at a temperature of from about −80° C. to about −45° C.

32. The process of claim 29, wherein the free base form of the compound of formula 3 is prepared from an acid addition salt of the compound of formula 3.

33. The process of claim 32, wherein the acid addition salt of the compound of formula 3 is a trifluoroacetic acid addition salt.

34. The process of claim 29, wherein the sulfonium methylide is dimethylsulfonium methylide.

35. The process of claim 29, wherein the reaction is carried out in an ether solvent or mixtures thereof.

36. The process of claim 35, wherein the ether solvent is tetrahydrofuran or a mixture of tetrahydrofuran and dichloromethane.

37. The process of claim 30, wherein step (c) comprises catalytic hydrogenation.

38. The process of claim 37, wherein the catalytic hydrogenation is performed using a palladium/carbon catalyst.

39. The process of claim 38, wherein the palladium/carbon catalyst is 10% palladium/carbon.

40. The process of claim 39, wherein the catalyst is Johnson-Matthey type A 402028-10.

41. A process for preparing a compound of formula 3

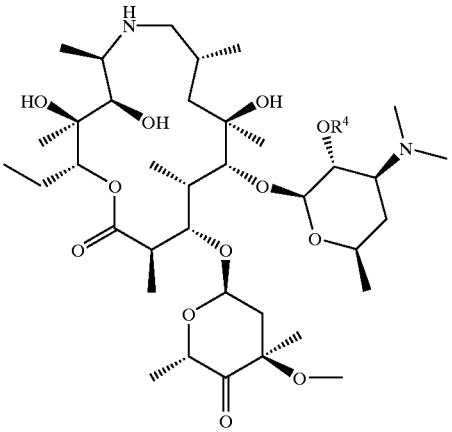

by oxidation of the C-4″ hydroxy group of a compound of formula 4

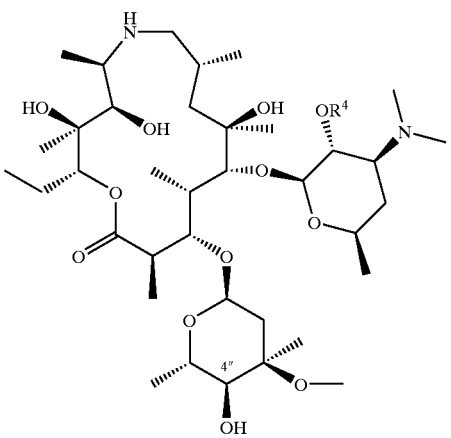

wherein $R^4$ is a hydroxy protecting group.

42. The process of claim 41, wherein the oxidation is performed by adding dimethylsulfoxide to a solution comprising the compound of formula 4 and a solvent, cooling the mixture to about −70° C., and then activating the dimethylsulfoxide in situ, and finally quenching the reaction.

43. The process of claim 42, wherein the temperature is maintained between −70° C. and −60° C. during until the reaction is quenched.

44. The process of claim 42, wherein the dimethylsulfoxide is activated using trifluoroacetic anhydride, oxalyl chloride, oxalyl chloride with trimethylsilylacetamide, polyphosphoric acid, pyridine.SO3, or acetic anhydride.

45. The process of claim 44, wherein the dimethylsulfoxide is activated using trifluoroacetic anhydride.

46. The process of claim 42, wherein the solvent is dichloromethane.

47. A process for preparing the trifluoroacetic acid

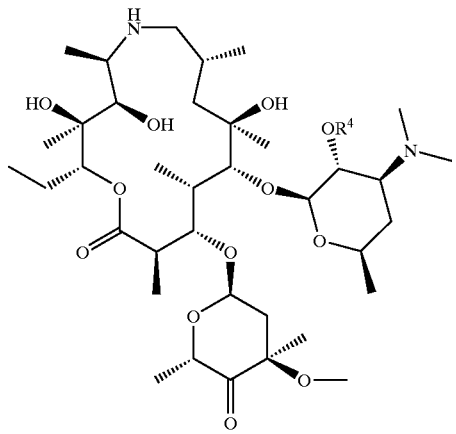

addition salt of a compound of formula 3 which comprises treating the compound of formula 3 with trifluoroacetic acid; and crystallizing the resulting acid addition salt;

wherein $R^4$ is a hydroxy-protecting group.

48. The process of claim 47, wherein $R^4$ is benzyloxycarbonyl.

49. The process of claim 47, wherein the acid addition salt is crystallized from isopropanol.

50. The process of claim 47, wherein the acid addition salt is crystallized from a mixture of methylene chloride and methyl tert-butyl ether.

51. The process of claim 41, wherein the compound of formula 4 is prepared by protection of the 2'-hydroxy group of the compound of formula 5

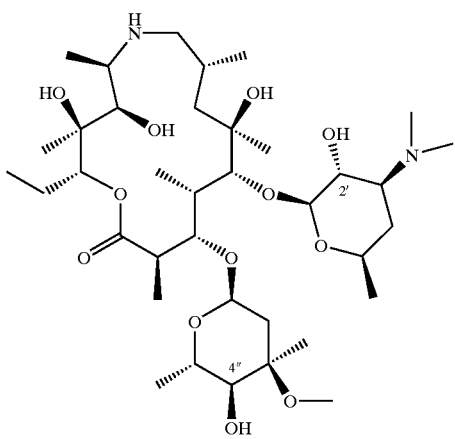

52. The process of claim 51, wherein the compound of formula 4 is carried forward directly to the oxidation step without isolation.

53. The process of claim 51, wherein the 2'-hydroxy group is protected with benzyloxycarbonyl.

54. The process of claim 53, wherein the benzyloxycarbonyl protecting group is prepared by reacting the compound of formula 5 with at least two molar equivalents of benzylchloroformate.

55. A trifluoroacetic acid addition salt of the compound of formula 3

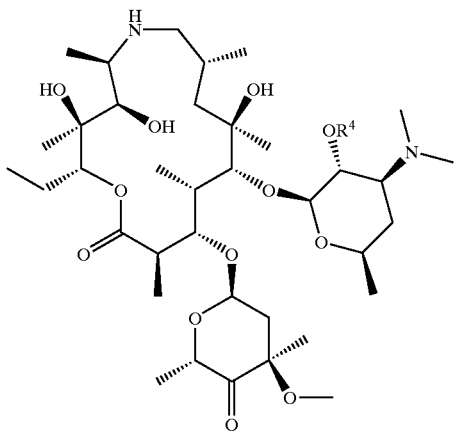

wherein $R^4$ is benzyloxycarbonyl.

56. The salt of claim 55, having the structure shown in formula 3a

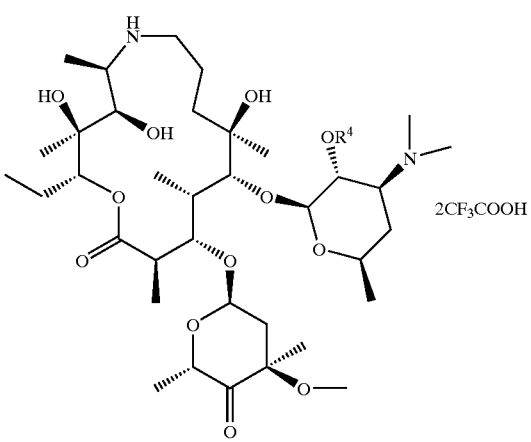

wherein $R^4$ is benzyloxycarbonyl.

57. A dibenzoyl-D-tartrate salt of the compound of formula 3

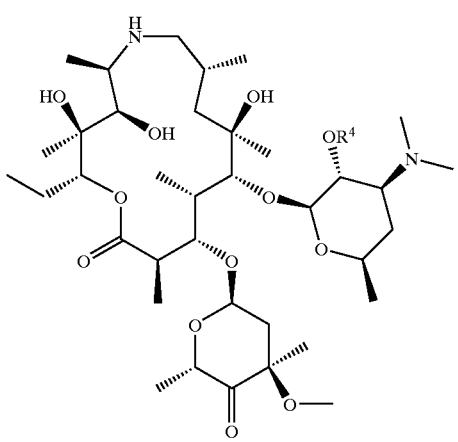

wherein $R^4$ is benzyloxycarbonyl.

* * * * *